United States Patent [19]

Ashmead et al.

[11] Patent Number: 4,725,427

[45] Date of Patent: Feb. 16, 1988

[54] EFFERVESCENT VITAMIN-MINERAL GRANULE PREPARATION

[75] Inventors: H. DeWayne Ashmead, Fruit Heights; Robert V. Petersen, Salt Lake City, both of Utah

[73] Assignee: Albion International, Inc., Clearfield, Utah

[21] Appl. No.: 589,152

[22] Filed: Mar. 13, 1984

[51] Int. Cl.$^4$ .................. A61L 9/04; A61K 31/59; A61K 31/28; A61K 31/30

[52] U.S. Cl. .................. 424/44; 514/23; 514/167; 514/168; 514/249; 514/251; 514/276; 514/345; 514/356; 514/387; 514/458; 514/474; 514/492; 514/494; 514/500; 514/502; 514/905

[58] Field of Search .................. 424/44, 280

[56] References Cited

U.S. PATENT DOCUMENTS

| | | | |
|---|---|---|---|
| 3,241,977 | 3/1966 | Mitchell et al. | 424/44 |
| 3,773,922 | 11/1973 | Gergely | 424/44 |
| 4,020,158 | 4/1977 | Ashmead et al. | 424/294 |
| 4,265,874 | 5/1981 | Bonsen et al. | 424/44 |
| 4,322,407 | 3/1982 | Ko | 424/280 |
| 4,436,720 | 3/1984 | Pakhomov et al. | 424/44 |

FOREIGN PATENT DOCUMENTS 46-4758  5/1971  Japan .................. 424/44

OTHER PUBLICATIONS

Chem. Abst. 80:52373(v) (1974)—Cruceanu et al.
Chem. Abst. 89 30826d (1978)—Tokes et al.
Chem. Abst. 90 76545k (1979)—Rafjnski et al.

*Primary Examiner*—Douglas W. Robinson
*Attorney, Agent, or Firm*—Thorpe, North & Western

[57] ABSTRACT

Flavored, effervescent, water soluble compositions containing water-soluble and oil-soluble vitamins and amino acid chelated minerals in bioavailable form are contained in a composition consisting of 20-30% of a vitamin blend consisting of water-soluble and oil-soluble vitamins adsorbed on a lactose carrier containing a minor amount of propylene glycol, 5-25% of one or more amino acid chelated minerals selected from the group consisting of calcium, magnesium, iron, zinc, copper and manganese, 20-45% citric acid, 5-25% of one or more alkali or alkaline earth metal bicarbonates or carbonates, 1-5% flavoring agent, 0.5-2% of a sweetening agent and sufficient additional lactose carrier to provide the desired vitamin and mineral content per unit dosage which will normally vary between about 2 and 6 grams. When dissolved in water a flavored, lightly carbonated drink is provided which will contain in soluble bioavailable form between about 50 to 100% of the U.S. RDA of one or more vitamins contained in a dosage unit of the composition and between about 20 to 50% of the U.S. RDA of one or more of the trace minerals iron, zinc, copper and magnesium as contained in a unit dosage of the composition as amino acid chelates. Separate effervescent vitamin compositions without minerals and mineral compositions without vitamins are also disclosed.

13 Claims, No Drawings

EFFERVESCENT VITAMIN-MINERAL GRANULE PREPARATION

BACKGROUND OF THE INVENTION

This invention relates to effervescent vitamin and mineral compositions for human consumption. More particularly, this invention relates to effervescent vitamin and mineral compostions which are completely soluble in water and provide desired quantities of vitamins and minerals in a readily bioavailable form.

With the current emphasis on health and fitness, there has arisen also an awareness of the need the human body has for proper nutrition. Particular emphasis has been placed on the need for adequate amounts of vitamins and minerals. Because of this the market has been flooded with a variety of vitamin and mineral products, each claiming to be superior in certain aspects.

Most vitamin and mineral preparations are formulated as capsules or tablets for human consumption. Others are added to foodstuffs as part of an enrichment or food supplement program. However, it is difficult to get small children to swallow capsules or tablets. In addition, many adults who are in need of vitamins and minerals suffer from physical conditions that make it difficult to swallow capsules or tablets. There are also situations where vitamin and mineral preparations are needed separate and apart from foodstuffs. Therefore, it is impractical to consume fortified foods just to obtain the value of their vitamin and mineral contents.

It has been suggested that vitamins, and sometimes minerals, be prepared in a water soluble form and utilized in beverages. One such suggestion is contained in U.S. Pat. No. 3,243,347 in which certain vitamins and minerals are absorbed on non fat dry milk solid granules which have been treated with propylene glycol. The product is said to dissolve in beverages such as milk, juices, tea, coffee and the like and is said to be odorless, tasteless and leave no after taste.

It is well established, however, that certain minerals are of limited solubility and often impart an objectionable odor and/or flavor to aqueous preparations. In addition, most minerals are provided in inorganic form and are at best difficult for the body to assimilate.

It is proposed in U.S. Pat. No. 3,526,494 to prepare a dry vitamin premix for introduction into milk utilizing lactose, the major component, of non fat milk solids, as the solubilizing agent. This patent also proposes prepackaging minerals separately from the vitamins for independent introduction into milk.

U.S. Pat. No. 4,268,529 teaches that metabolically available iron and ascorbic acid are unstable when combined but may be stabilized by the addition of gelatin.

There is considerable prior art relative to the production of vitamin mixtures for use in foods and/or beverages. Representative of these are U.S. Pat. Nos. 2,421,598; 2,375,279; 2,897,119 and 3,574,826.

It is now well documented that minerals are more bioavailable if administered in the form of chelates wherein the chelating ligands are amino acids or protein hydrolysates. Typical patents demonstrating this concept are U.S. Pat. Nos. 3,873,296; 3,969,540 and 4,020,158. These chelated minerals are known in the art by various names such as metal proteinates, amino acid chelates and peptide or polypeptide chelates. These will be referred to herein simply as "amino acid chelates" which is the term predominately used in the market place. According to the above patents, amino acid chelates are relatively insoluble at a basic pH and may be incompletely formed at an acid pH. U.S. Pat. Nos. 4,216,143 and 4,216,144 teach soluble amino acid chelates which may be obtained in powdered form and subsequently redissolved in water for human and animal use. These amino acid chelates are stated to be soluble over a relatively narrow pH range of between about 7 and 8. The use of a specific combination of iron, copper and molybdenum, amino acid chelates absorbed onto a proteinaceous food carrier for treatment of iron deficiency anemia is taught in U.S. Pat. No. 4,208,405. This patent also teaches that other nutritional supplements, such as vitamins, can also be adsorbed on the food carrier. However, there is no teaching of combining vitamins and minerals, in the form of amino acid chelates, in a single water soluble composition.

It would be desirable to be able to provide a combination of vitamins and minerals in a water soluble form wherein the various vitamins and minerals in the mixture are compatible and readily bioavailable. However, at the present time most available formulations sacrifice bioavailability to obtain a compatible solution or sacrifice compatibliity and market the minerals and vitamins separately. In the alternative, vitamins and minerals have been adsorbed onto foodstuff carriers. This provides bulk and makes them inconvenient to take.

OBJECTS AND BRIEF SUMMARY OF THE INVENTION

It is an object of the present invention to provide a vitamin mineral combination that is completely soluble in water wherein both the vitamins and minerals are readily bioavailable.

It is also an object of the present invention to provide a flavored vitamin mineral combination in the form of granules, tablets or powders which effervesce in water to provide a pleasant tasting drink which may be readily consumed to provide the consumer with desired amounts of vitamins and minerals in bioavailable form.

A still further object of this invention is to provide a composition consisting of required vitamins and minerals, wherein the minerals are in the form of soluble amino acid chelates, in combination with effervescing ingredients in a stable and compatible form.

These and other objects may be realized by means of an effervescing composition formulated in a specific manner so as to contain vitamins and amino acid chelated minerals in a water soluble, compatible, bioavailable form.

The composition making up the granules, tablets or powders is first formed in portions consisting of a dry vitamin premix and a separate dry amino acid chelate mineral premix. The two premixes are then blended along with appropriate flavoring and effervescing materials and packaged in air tight and moisture tight containers.

The vitamin premix is formulated in a two step process. In the first step the water soluble vitamins, such as calcium ascorbate, folic acid, thiamine mononitrate, riboflavin-5-phosphate sodium salt, niacinamide, pyridoxine HCl, biotin and calcium pantothenate are dry-blended, screened and blended with powdered lactose wherein the lactose comprises the major portion of the mix.

A second vitamin mix, consisting of the oil and alcohol soluble vitamins is formed. The solvent for this mix is a mixture of ethyl alcohol containing a minor amount of propylene glycol. Into this solvent is dissolved desired amounts of Vitamin A Palmitate in oil, Vitamin $D_2$ in oil and Vitamin E (d-1 alpha tocopherol acetate) in oil.

About one part per weight of the alcohol solution mix is blended with about ten parts by weight of the dry vitamin-lactose mix with agitation. The mixture when thoroughly blended is air dried and screened to provide the vitamin premix.

A separate mixture consisting of dry, finely divided water soluble amino acid chelates is provided. The minerals involved are subject to variation as to the number of minerals and mineral concentration of each and may consist of one or more minerals preferably selected from the group consisting of calcium, zinc, iron, magnesium, manganese and copper.

The vitamin premix and mineral premix are then dry blended together in appropriate ratios.

The vitamin-mineral mixture thus prepared is blended with a predetermined amount of anhydrous citric acid powder.

To this mixture is added minor amounts of flavoring and sweetening agents. Preferably the sweetening agent will be aspartame, although thaumatin, saccharin and saccharin salts may also be utilized. Flavoring agents having fruit flavors are preferred.

Appropriate amounts of alkali or alkaline earth metal bicarbonates or carbonates such as potassium and/or sodium bicarbonate are blended into the mixture at the time the citric acid is added or are added separately after the addition of the flavoring and sweetening agents.

After all these ingredients are added, the mixture is thoroughly blended and brought to the desired volume and concentration by the addition of lactose powder.

The composition may be utilized as a powder or may be formed into granules or tablets by conventional technology. When used as a powder or in granulated form, the composition may be packaged in bulk or in individual dosage size serving packets.

When formed into tablets appropriate tableting aids such as binders and lubricants may be added to the composition.

When made into granules, the mixture is moistened with an appropriate amount of ethanol and is wet granulated through the desired mesh screen and air dried. The dried granules are then packaged in air tight and moisture tight containers for use. Preferably the containers will be foil pouches of individual size dosages ranging from about two to six grams.

For use, a dosage unit amount is deposited in a desired amount of water. The citric acid-bicarbonate or carbonate combination causes the composition to effervesce with the release of carbon dioxide. The flavoring and sweetening agent provide a soft drink flavor to the resulting solution which contains the dissolved minerals and vitamins in a pleasant tasting and bioavailable form.

While there is considerable prior art dealing with effervescent medicinal preparations, it is directed almost entirely to analgesic compositions containing acetyl salicylic acid and its salts. Some mention is also made of such formulations containing ascorbic acid and a thiamine salt. Typical prior art is found in U.S. Pat. Nos. 1,526,981; 2,540,253; 2,985,562; 3,024,165; 3,772,430 and 3,773,922. Of particular interest is U.S. Pat. No. 4,083,951 which teaches effervescent combinations of acetyl salicylates with ferrous ions. This patent teaches separating the salicylate from the ferrous salt stating that these components should not be in intimate contact until placed in water just prior to ingestion.

DETAILED DESCRIPTION OF THE INVENTION

The invention as summarized above lies primarily in the discovery that the vitamins and amino acid chelated minerals, as combined to provide effervescent composition are stable, compatible and, when dissolved in water, are readily bioavailable. The exact proportions or ratios of one vitamin to another, one mineral to another, or vitamins to minerals is not novel and is well within the knowledge of those skilled in the art. The United States Government has established recommended daily allowances for most essential vitamins and minerals (U.S. RDA) and a portion or all of these allowances may be contained in each serving portion of the granules of this invention.

It is not, therefore, the intent to discuss or explain the need for each vitamin or mineral to be utilized. What is important is that the vitamin or mineral be made available in a form which may be readily assimilated into biological tissues. Otherwise, no matter how much of a preparation is consumed it would be of limited or no benefit.

Not every preparation will contain all essential vitamins or minerals. Hence, the number of vitamins and minerals in an effervescent granule is not determinative of its novelty.

Vitamins are usually distinguished or classified as being water-soluble or fat-soluble. The fat-soluble vitamins are the A,D,E and K vitamins and are usually measured in International Units(IU). They are generally administered in an oil base. The water-soluble vitamins are the C and various B vitamins and are measured in milligrams.

The minerals capable of forming amino acid chelates for which a U.S. RDA has been established are calcium, iron, magnesium, zinc and copper. Manganese is also considered essential although no U.S. RDA has been established. In addition, other chelatable minerals such as cobalt, vanadium, molybdenum, tin, nickel, selenium and chromium are also considered to play essential roles in life's processes. Any or all of these metals, as amino acid chelates, may be utilized in the present invention.

The invention will now be described with reference to the formulation of each component mixture to be utilized in the preparation of the composite effervescent vitamin-mineral composition.

VITAMIN PREMIX

Preparation of Water-Soluble Vitamin Mixture

This mixture is prepared by dryblending the various ingredients in powdered form. The vitamins to be blended may be in various forms. For example, one may obtain Vitamin C in the form of ascorbic acid or calcium ascorbate. Similarly, one may use niacin in the form of nicotinic acid or niacinamide. Pantothenic acid or calcium pantothenate may be utilized. Thiamine may be used at the mononitrate or hydrochloride salt. Riboflavin may be added in the free form or as a phosphate salt.

Whatever molecular form of vitamin is used it is essential that it be in powdered form. The vitamins will be selected from the group consisting of Vitamin C and any or all of the vitamins making up the B complex. B complex vitamins include thiamine ($B_1$), riboflavin ($B_2$), niacin ($B_3$), pyridoxine ($B_6$), pantothenic acid ($B_5$), folic acid, biotin, choline, para-amino benzoic acid and inositol. Cobalamin ($B_{12}$) may added with the water soluble vitamins or along with the fat-soluble ones as described below.

The powdered water soluble vitamins are blended and screened through about a 20 mesh (0.84 mm) screen. The dry screened vitamins are then blended with powdered lactose to the desired concentration. Typically the mixture will consist of about 10-40% vitamins and 60-90% lactose on a weight basis.

Preparation of Fat-Soluble Vitamin Solution

In a separate container the fat-soluble vitamins are dissolved in an alcohol solvent consisting of ethanol and propylene glycol. The solvent will consist of a major portion of ethanol and a minority of propylene glycol. Typically about 20-40% will be propylene glycol with 60-80% being ethanol. Into this solvent is dissolved appropriate amounts of fat-soluble vitamins as oil solutions. Vitamin A palmitate, Vitamin $D_2$, Vitamin E from any source such as d-alpha tocopherol, d-1 alpha tocopherol acetate, and Vitamin K may be added in desired portions. The concentrations of vitamins in their oil solutions may vary as may the amounts of oil added to the alcohol solvent. Generally speaking, the solvent will comprise the major portion of the dissolved mixture and may vary from about 50 to 75% of the mixture with the oil containing the vitamins comprising from about 25 to 50%. If desired, small amounts of Vitamin $B_{12}$ (cobalamin) may be dissolved in this solution.

Appropriate amounts of the oil soluble vitamins dissolved in the alcohol solvent are then blended with the mixture of the dry water-soluble vitamins. Typically the combination of fat-soluble and water-soluble vitamins will be sufficient that one gram of the resulting powdered mixture will provide up to 100% of the U.S. RDA of the vitamins involved. However, other amounts are also within the scope of the invention.

In order to provide the above concentrations, the amount of oil-alcohol mixture blended with the dry vitamin-lactose mixture will vary from about 5 to 15% by weight. Once mixed and thoroughly blended this vitamin premix is air dried thereby driving off a major portion of the ethanol. The resulting powdered mixture is screened through a larger screen than used for the dried water-soluble vitamin-lactose mixture and stored in air and water tight containers for subsequent blending with additional ingredients. A 16 mesh screen (1 mm) has been found to be adequate.

The dryness and flowability of the mixture may be regulated by controlling the amount of propylene glycol used in dissolving the fat-soluble vitamins.

When dry this premix will generally consist of about 45-85% lactose, 1-2% propylene glycol with the remainder being adsorbed vitamins and oil.

AMINO ACID CHELATE MIXTURE

The prior art referenced above is adequate to provide sufficient data regarding the preparation of amino acid chelates. Briefly, in order for a true chelate to be formed the mole ratio of protein hydrolysate ligand or amino acid ligand to metal must be at least 2:1 and the reaction conditions must favor the formation of a chelate by the removal of potentially interferring protons.

Depending upon the ligand used the molecular weight of any amino acid chelate may vary greatly. For example, the weight ratio of metal to ligand will be greatest if using pure glycine, the simplist amino acid, as the ligand. However, if using a polypeptide at the chelating ligand the ratio of metal to ligand will be greatly diminished. Therefore, the amount of amino acid chelate to be blended with the vitamin premix will vary greatly depending upon the number of metals utilized and the metal concentration. Since macrominerals such as calcium and magnesium may be obtained from other sources more easily than trace minerals such as copper, zinc, manganese and iron the amino acid chelate mixture will give preference to the trace minerals. It is desired that the trace minerals will be present in amounts of about 20 to 50% of the U.S. RDA per unit dosage. In order to obtain this dosage the effervescent composition will normally contain between about 5-25% by weight amino acid chelates.

By utilizing preparation techniques such as described in U.S. Pat. Nos. 4,216,143 and 4,216,144, soluble amino acid chelates can be prepared for use in the present invention.

EFFERVESCENT VITAMIN-MINERAL GRANULE PREPARATION

The powdered vitamin premix and amino acid chelate mixture are combined in desired proportions and thoroughly blended to provide predetermined amounts of vitamins and minerals for each dosage unit of two to six grams.

The remaining ingredients, except the lactose filler which is added last, may be blended in any desired order. Therefore, the following order is exemplary only and may be rearranged to meet the operational facilities in which the formulation is prepared.

To the blended vitamin and mineral mixture is added a combination of citric acid, potassium and/or sodium bicarbonates, flavoring agents and sweeteners. The amount of flavoring agents and sweeteners used are subject to considerable variations and will not be more than necessary to provide the desired flavor and sweetness to be released from the composition when dissolved in water. Typically the flavoring agent will comprise between about 1 to 5% by weight of the granular formulation. Fruit flavors are desirable and may be selected from a wide variation of citrus and non-citrus fruits and berries. The particular flavor utilized is not critical to the proper functioning or the invention as long as it imparts a desirable flavor to the final product. Flavors such as lemon, lime, orange, grapefruit, apple, peach, apricot, cherry, raspberry, strawberry and grape may be utilized as may tropical fruits. Combinations of various flavors may also be useful.

The sweetening agent is preferably one which is non-nutritive or low in calories. In other words, it is preferable to avoid sucrose, glucose and other saccharides except for the lactose which is utilized. Because of its strong sweetening power and acceptability by consumers and government agencies, it is preferred to use aspartame as the sweetening agent. However, where acceptable, other synthetic sweetening agents such as thaumatin, saccharin and saccharin salts may also be employed. The sweetening agent will normally comprise between about 0.5 to 2% of the total formulation.

Citric acid powder is present in significant concentrations. Approximately 20 to 45% of the total formulation will consist of citric acid powder. This provides sufficient acid to react with the bicarbonate salts to release carbon dioxide through effervescence. In addition, any excess citric acid renders the resulting effervescent solution of vitamins and minerals acidic which enhances the fruit flavor of the product.

The bicarbonate salt may be either sodium or potassium bicarbonate or a mixture. Also, other salts capable of releasing carbon dioxide in the presence of an acid may also be utilized. Typically, any suitable alkali or alkaline earth bicarbonate or carbonate may be utilized. These bicarbonate or carbonate salts are preferably present in amounts ranging from about 5 to 25% of the granular formulation. A particularly preferred combination consists of about 60% potassium bicarbonate and 40% sodium bicarbonate. This limits the amount of sodium ions in the resulting vitamin- mineral solution. The citric acid is preferably first blended with the vitamin and mineral mixture. The flavoring and sweetening agents may then be added followed by addition of the carbonate or bicarbonate salts. In the alternative, the bicarbonates or carbonates may be blended in with the citric acid powder followed by the addition of the flavoring and sweetening agents.

When appropriate amounts of these have all been blended, lactose powder is added as a filler to provide the final formulation having the desired concentration of vitamins and minerals. Typically, sufficient lactose is added such that about a two to six gram dose of the total formulation will provide up to 100% of the U.S. RDA of one or more vitamins and up to 50% of the U.S. RDA of one or more trace minerals. Generally, this requires adding between about 5 to 25% lactose based on the weight of the total formulation. This is in addition to the lactose utilized in preparing the vitamin premix as previously described. The powdered formulation thus obtained may be utilized, as is, or may be further formulated into granules or pressed into tablets. In addition, other ingredients such as preservatives, antioxidants or other additives may be incorporated into the formulation.

The actual amount of vitamins and minerals in each dosage unit of effervescent composition may vary greatly. Some people subscribe to the "more is better" theory and consume great quantities of vitamins and minerals. It is possible to prepare the composition so as to contain mega dosages if desired. However, it is preferable to formulate the composition to contain between 50 to 100% of the U.S. RDA of one or more vitamins and 20-50% of the U.S. RDA of one or more trace minerals such as iron, zinc, manganese and copper. No U.S. RDA has been established for manganese. However, the Food and Nutrition Board of the National Academy of Sciences-National Research Council in 1979 proposed an RDA for manganese of 4.0 mg. For purposes of this disclosure that dosage shall be considered to be a U.S RDA for manganese. The scope of the invention however, should not be limited solely to the above ranges and is deemed to extend to any effervescent water soluble combination of vitamins and amino acid chelates formulated as described herein.

As previously stated, a dosage unit will normally consist of about two to six grams. When used as a powder, the formulation will be packed in containers of any desired size. A ladle or scoop measure holding a unit size dose may be included. Preferably, the container will contain a tight fitting lid to keep excess air and moisture from entering the composition.

Tablets can be pressed into the desired dosage unit size. In some instances, it may be desirable to have tablets in smaller sizes such that two or more tablets comprise a unit dosage. Appropriate tableting aids such as binders, lubricants and the like may be utilized in pressing the tablets. Tablets can be packaged in unit size dosages such as foil pouches or be packaged in quantities in bottles or cans.

When the composition is to be made into granules, the following procedure may be followed.

The powder is granulated by being moistened with about to 15% by weight of ethanol. When damp, this product is sieved through a 6 to 10 mesh seive (3.4 to 1.7 mm) and dried. The dried granules are again screened through an appropriate sieve to break up any agglomeration and packaged in moisture tight containers. Preferably such packaging will be in dosage sized foil pouches holding 2-6 and preferably, about 4 grams of granules.

Whether packaged in bulk, i.e., in cans or bottles, or in dosage sized pouches, it is imperative that these packages be moisture proof and that the composition be thoroughly dried to prevent interaction of the citric acid and bicarbonate salts which would result in the release of carbon dioxide gas.

For use, a dosage unit of the product need merely be added to an appropriate amount of cold water, i.e. 6-8 fluid ounces, and allowed to dissolve accompanied by the release of carbon dioxide through effervescence. The effervescent action uniformly disperses all ingredients in the formulation and aids in keeping all of the various vitamins and minerals in solution.

The fact that the minerals are chelated minimizes any interference between the vitamins and minerals. For example, ascorbic acid and ferrous ions are known to be incompatible in aqueous solutions. However, with amino acid chelation, the positive charges on the ferrous ion are neutralized providing two advantages. One, the ions are not free to interact with the ascorbic acid. Two, the ferrous amino acid chelate is much more bioavailable then the ferrous ion alone and is assimilated into the body much more rapidly and to a greater degree. The same reasoning is believed to apply to all of the amino acid chelates utilized regardless of which metal ion is employed. With the positive charge on the metal ions eliminated or at least minimized the stability and palatability of the effervescent formulation is greatly enhanced.

The composition, as formulated, contain all ingredients in a stable, water soluble form. The amino acid chelates appear to retain their integrity as chelates, even in the acid environment created by the use of excess citric acid and in the presence of the carbonic acid formed during the release of carbon dioxide through effervescense. Citric acid and ascorbic acid are also known chelating agents and also function as ligands in keeping the metal ions neutralized and in a bioavailable, water soluble form.

The pH of the solution after a unit dosage of composition has been dissolved therein may be regulated by the ratio of citric acid to bicarbonate contained in the composition. An excess of citric acid plus the release of carbon dioxide into the solution will obviously contribute to an acid pH. However, by having an excess of bicarbonate ions, the pH may be raised to a neutral or even basic pH if desired.

Other modifications may also be made without departing from the scope of the invention. It may be desirable to make a composition containing only vitamins or only minerals. If so, the above description would be modified by removing either the vitamin preblend or the amino acid chelated minerals from the formulation and the remainder of the ingredients would be adjusted accordingly. For vitamins, a dosage size unit would be lowered to about one to four grams. The total vitamin content of the formulation would vary between about 25 to 50% of the total formulation with the relative percentages of citric acid, carbonates or bicarbonates, flavoring agents, sweetening agents and added lactose being the same as described above. For mineral, the total amino acid chelate content of the preparation would vary between about 5 to 50% and the dosage units could vary from about one to six grams. The percentage range of other ingredients would remain as stated above.

The invention may be illustrated with reference to the following examples.

EXAMPLE I

A powdered mixture of water soluble vitamins was prepared by blending a mixer 1,150 grams of calcium ascorbate, 4.55 grams of folic acid, 25.5 grams of thiamine mononitrate, 36.78 grams of the sodim salt of riboflavin-5-phosphate, 340.5 grams of niacinamide, 41.2 grams of pyridoxine HCl, 3.4 grams of biotin and 133.38 grams of calcium pantothenate. These blended materials were screened through a 20 mesh screen and then blended with 8,513 grams of powdered lactose.

In a separate container containing 595 cc of 95% ethanol and 188 cc of propylene glycol was added 27.23 grams of a vegetable oil solution containing 1,000,000 IU of Vitamin A Palmitate and 200,000 IU of Vitamin D per gram, 16.43 grams of a vegetable oil solution containing 1,724,800 IU per gram of Vitamin A Palmitate, 408.63 grams of an oil solution containing 1000 IU of Vitamin E (d-1 alpha tocopherol acetate) per gram and 0.103 grams of cyanocobalamin. This solution was mixed until all ingredients were dissolved.

The solution of oil soluble vitamins was added slowly to the dry water soluble vitamin mixture with constant agitation until all had been added and was thoroughly blended. The resulting mixture was damp and was air dried at ambient temperature. When dried it was screened through a 16 mesh screen and weighed approximately twenty five pounds or 11 35 kilograms. The concentration was such that one gram of formulation contained the U.S. RDA of each vitamin included.

To the above 25 pound mixture was added 18 lbs. 1 oz. of a mixture of iron, zinc, magnesium, calcium and manganese amino acid chelates and potassium amino acid complex. The proportion of metals were such that 0.72 grams of this mixture contained 25% of the U.S. RDA of iron and zinc, 4% of the U.S RDA of magnesium, 2% of the U.S. RDA of calcium and 1.25 mg of manganese and 90 mg of potassium.

After being thoroughly blended there was added to this mixture 35 pounds of powdered anhydrous citric acid followed by a mixture consisting of 5.75 pounds of potassium bicarbonate and 3.75 pounds of sodium bicarbonate. This mixture was thoroughly blended and then there was added 3 pounds of lime flavoring powder and 1 pound of lemon flavoring powder along with 0.75 pounds of aspartame sweetener. After again completely mixing the compositions was completed with the addition of 7.69 pounds of lactose. The final composition consisted of approximately 100 pounds.

This composition was granulated by adding 12 pounds of 95% ethyl alcohol and, while wetted, was passed through an 8 mesh screen and air dried at ambient temperature. The dried granules were screened through a 10 mesh screen and packaged in foil pouches containing approximately 4 grams per pouch.

The granules dissolved easily and completely when placed in 6 fluid ounces of cold water to provide a pleasant tasting, lightly carbonated lemon-lime flavored drink containing the above-mentioned concentrations of vitamins and minerals.

EXAMPLE II

The above procedure is followed adding copper amino acid chelate to the formulation in amounts sufficient to provide 25% of the U.S. RDA per 4 grams of granules and utilizing 9.5 pounds of potassium bicarbonate instead of a mixture of potassium and sodium bicarbonates.

EXAMPLE III

The procedure of Example I is again followed utilizing protein hydrolysates having lower molecular weights as ligands. The same metal concentration as in Example I was then contained in 10.5 pounds of amino acid chelates and the final composition was made by adding 15.25 pounds of lactose to make a total composition containing 100 pounds.

EXAMPLE IV

A composition as in Example I is again prepared wherein the amounts of vitamins are cut in half and the amounts of trace minerals in the amino acid chelates are doubled causing the composition to contain 50% of the U.S. RDA of both vitamins and the trace minerals iron and zinc.

EXAMPLE V

Following the procedure outlined in Example I, a powder is prepared leaving out the amino acid chelates. The effervescent powder therefore contains only vitamins and has no added chelated minerals. The composition is pressed into tablets using magnesium stearate as a tableting aid and has a unit dosage size of 2.3 grams. This composition consists of 43% vitamin premix, 35% citric acid, 9.5% potassium and sodium bicarbonates, 4% lemon and lime flavoring agents, 1% aspartame and 7.5% added lactose.

EXAMPLE VI

The procedure of Example I is again followed to prepare a powder containing amino acid chelated minerals and no added vitamins. The amino acid chelates comprise 43% for the total powdered formulation which has a unit dosage size of 1.7 grams. The percentage of other ingredicednt remains the same as in Example I and V. The product is stored in bulk in cans having air tight lids. A measuring scoop holding a dosage unit is utilized to determine the amount of effervescent powder to be added to a glass of water for use.

The above examples are considered to adequately disclose the basic features of the invention and the mode by which they may be carried out. It is obvious that any desired concentrations of vitamins and minerals in the form of amino acid chelates may be incorporated into the effervescent compositions as long as there are sufficient amounts of lactose, propylene glycol, citric acid and bicarbonate salts to provide the vitamins and minerals in a soluble and effervescent form when the composition is placed in water. Therefore, the scope of the invention should be limited only by the following claims.

We claim as our invention:

1. An effervescent vitamin and mineral composition in water soluble form consisting of:
   (a) 20–30% by weight of a dry mixture of water-soluble vitamins selected from the group consisting of Vitamin C, Vitamin $B_1$, Vitamin $B_2$, Vitamin $B_3$, Vitamin $B_5$, Vitamin $B_6$, folic acid, biotin, choline, para-amino benzoic acid and inositol, and oil soluble vitamins selected from the group consisting of Vitamin A, Vitamin $D_2$, Vitamin E and Vitamin K, said mixture containing, in addition to said vitamins, about 45–85% by weight lactose and 1–2% by weight propylene glycol,
   (b) 5–25% by weight of one or more essential minerals selected from the group consisting of calcium, magnesium, copper, zinc, iron and manganese in the form of amino acid chelates,
   (c) 20–45% by weight powered citric acid,
   (d) 5–25% by weight of a powdered alkali metal or alkaline earth metal bicarbonate or carbonate,
   (e) 1–5% by weight of a flavoring agent,
   (f) 0.5–2% by weight of a sweetening agent, and
   (g) sufficient additional lactose to bring the composition to 100%.

2. An effervescent vitamin and mineral composition as in claim 1 wherein a dosage unit of said composition is about two to six grams.

3. An effervescent vitamin and mineral composition as in claim 1 wherein a dosage unit of said composition contains between about 50 and 100% of the U.S. RDA of one or more vitamins included in the composition and between about 20 and 50% of the U.S. RDA of one or more of the trace minerals selected from the group consisting of zinc, copper, iron, and manganese contained in the composition.

4. An effervescent vitamin and mineral composition as in claim 1 wherein the composition is in the form of granules.

5. An effervescent vitamin and mineral composition as in claim 1 wherein the composition is in the form of tablets.

6. An effervescent vitamin and mineral composition as in claim 1 wherein said alkali or alkaline earth bicarbonate or carbonate is a member selected from the group consisting of potassium bicarbonate and sodium bicarbonate and mixtures thereof.

7. An effervescent vitamin and mineral composition as in claim 1 wherein said sweetening agent is a member selected from the group consisting of aspartame, saccharin and a saccharin salt.

8. An effervescent vitamin and mineral granular composition as in claim 7 wherein the sweetening agent is aspartame.

9. A method of preparing an effervescent, water soluble composition water-soluble and oil-soluble vitamins and amino acid chelated minerals comprising the steps:
   (a) blending together a mixture of water-soluble vitamins selected from the group consisting of Vitamin C, Vitamin $B_1$, Vitamin $B_2$, Vitamin $B_3$, Vitamin $B_5$, Vitamin $B_6$, folic acid, biotin, choline, para-amino benzoic acid and inositol in powdered form with powdered lactose to obtain a mixture consisting of about 10–40% water soluble vitamins and 60–90% lactose,
   (b) dissolving an oil solution of fat soluble vitamins selected from the group consisting of Vitamin A, Vitamins $D_2$ Vitamin E and Vitamin K in a alcoholic solvent consisting of 60–80% ethyl alcohol and 20–40% propylene glycol,
   (c) blending said water-soluble vitamin-lactose mixture with said alcoholic solvent solution containing fat soluble vitamins and air drying the resulting mixture to produce a powdered vitamin premix consisting of about 13–54% water-soluble and oil-soluble vitamins, 1–2% propylene glycol and 45–85% lactose,
   (d) blending together in powdered form sufficient vitamin premix and a mixture of one or more amino acid chelated minerals wherein the mineral is selected from the group consisting of calcium, magnesium, iron, zinc, copper and manganese and mixtures thereof to provide a vitamin and mineral blend,
   (e) admixing said vitamin and mineral blend with powered citric acid, one or more members selected from the group consisting of a powdered alkali or alkaline earth carbonate or bicarbonate, one or more powdered flavoring agents and one or more sweetening agents and blending therein additional lactose to provide an effervescent vitamin and mineral powder consisting of 20 to 30% of said vitamin premix, 5–25% of said amino acid chelates, 20–45% citric acid, 5–25% of said alkali or alkaline earth metal bicarbonate or carbonate, 1–5% flavoring agents, 0.5–2% sweetening agents with the balance being added lactose.

10. A method of preparing an effervescent, water soluble composition as in claim 9 wherein said composition is packaged in dosage size units containing about 2 to 6 grams.

11. A method of preparing an effervescent, water soluble composition as in claim 10 wherein each dosage size unit contains about 50 to 100% of the U.S. RDA of one or more of the vitamins contained therein and about 20 to 50% of the U.S. RDA of one or more of the trace minerals iron, zinc, copper and magnesium as contained therein as amino acid chelates.

12. A method of preparing an effervescent, water soluble composition as in claim 9 wherein the effervescent powder obtained is formulated in the form of granules by wetting said powder with ethyl alcohol and passing said wetted powder through a sieve to form said granules followed by air drying.

13. A method of preparing an effervescent, water soluble composition as in claim 9 wherein the effervescent powder obtained is formulated in the form of tablets by pressing said powder with appropriate tableting aids in a press.

* * * * *